United States Patent [19]

Neustadt

[11] Patent Number: 5,407,960

[45] Date of Patent: Apr. 18, 1995

[54] MERCAPTOCYCLOACYL AMINOACID ENDOPEPTIDASE INHIBITORS

[75] Inventor: Bernard R. Neustadt, West Orange, N.J.

[73] Assignee: Schering Corporation, Kenilworth, N.J.

[21] Appl. No.: 859,727

[22] PCT Filed: Dec. 20, 1990

[86] PCT No.: PCT/US90/07353

§ 371 Date: Jun. 11, 1992

§ 102(e) Date: Jun. 11, 1992

[87] PCT Pub. No.: WO91/09840

PCT Pub. Date: Jul. 11, 1991

[51] Int. Cl.[6] .................................. A01N 37/18
[52] U.S. Cl. ............................. 514/613; 514/616; 558/250; 562/426; 562/556; 560/16; 560/147; 564/162; 568/25; 568/61; 568/67
[58] Field of Search .................... 558/250; 568/61, 25, 568/67; 514/12, 13, 613, 616; 530/324, 326; 562/426, 556; 564/162; 560/16, 147

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,256,761 | 3/1981 | Suh et al. | 424/282 |
| 4,329,495 | 5/1982 | Bindra | 562/426 |
| 4,344,949 | 8/1982 | Hoetle et al. | 424/258 |
| 4,350,704 | 9/1982 | Hoetle et al. | 424/274 |
| 4,374,829 | 2/1983 | Harris et al. | 424/177 |
| 4,374,847 | 2/1983 | Gruenfeld | 424/274 |
| 4,401,677 | 8/1983 | Greenberg et al. | 424/317 |
| 4,410,520 | 10/1983 | Watthey | 424/244 |
| 4,462,943 | 7/1984 | Petrillo et al. | 260/112.5 R |
| 4,468,519 | 8/1984 | Krapcho | 548/409 |
| 4,470,972 | 9/1984 | Gold et al. | 424/177 |
| 4,470,973 | 8/1984 | Natarajan et al. | 424/177 |
| 4,508,729 | 4/1985 | Vincent et al. | 514/419 |
| 4,512,924 | 4/1985 | Attwood et al. | 260/243.3 |
| 4,513,009 | 4/1985 | Rogues et al. | 514/513 |
| 4,555,506 | 11/1985 | Karanewsky et al. | 514/113 |
| 4,610,816 | 9/1986 | Berger | 549/452 |
| 4,740,499 | 4/1988 | Olins | 514/13 |
| 4,774,256 | 9/1988 | Delaney et al. | 514/513 |
| 4,801,609 | 1/1989 | Haslanger et al. | 514/506 |

FOREIGN PATENT DOCUMENTS 274234 7/1988 European Pat. Off.
2218983 11/1989 United Kingdom.

*Primary Examiner*—José G. Dees
*Assistant Examiner*—Joseph M. Conrad, III
*Attorney, Agent, or Firm*—Anita W. Magatti; Eric S. Dicker

[57] ABSTRACT

Mercaptocycloacyl aminoacid inhibitors of endopeptidase of the formula

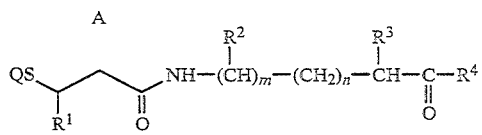

or a pharmaceutically acceptable salt thereof, alone or in combination with an ACE inhibitor or an ANF, in the treatment of cardiovascular disorders such as hypertension, congestive heart failure, edema and renal insufficiency, and treatment of nephrotoxicity pain conditions, and pharmaceutical compositions containing said compounds are disclosed.

11 Claims, No Drawings

MERCAPTOCYCLOACYL AMINOACID ENDOPEPTIDASE INHIBITORS

BACKGROUND OF THE INVENTION

The present invention relates to mercaptoacyl aminoacid inhibitors of endopeptidases useful in the treatment of cardiovascular disorders and pain conditions.

Cardiovascular conditions which may be treated with compounds of the present invention include hypertension, congestive heart failure, edema and renal insufficiency.

Human hypertension is a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. Enkephalin is known to be inactivated by a group of naturally occurring enzymes known as enkephalinases or endopeptidases.

A variety of compounds known as endopeptidase inhibitors are useful as analgesics and/or in the treatment of hypertension. For example, European Patent Application 274,234 discloses, inter alia, spiro-substituted glutaramide diuretic compounds of the formula

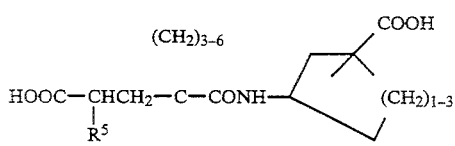

wherein $R^5$ may be a variety of alkyl or amino derivatives or a heterocycle.

European Patent Application 38,046 discloses, inter alia, enkephalinase inhibitors of the formula

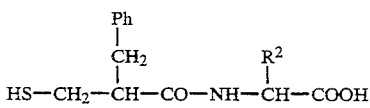

wherein $R^2$ is lower alkyl or methylthiomethyl and Ph is optionally substituted phenyl. U.S. Pat. No. 4,329,495 discloses specific chiral compounds of a similar scope.

U.S. Pat. No. 4,513,009 discloses, inter alia, alpha amino acid derivatives of the formula

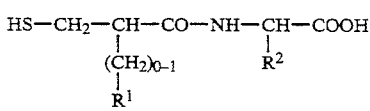

wherein $R^1$ is cyclohexyl and $R^2$ is preferably hydrogen, alkyl, benzyl or benzyloxyalkyl. The compounds are said to have enkephalinase inhibiting and hypotensive activity. U.S. Pat. No. 4,401,677 discloses similar analgesic compounds wherein $R^1$ is lower alkyl. U.S. Pat. No. 4,740,499 discloses the use of thiorphan (a compound within the scope of U.S. Pat. No. 4,513,009) to enhance the activity of an atrial peptide.

U.S. Pat. No. 4,053,651 discloses angiotensin converting enzyme (ACE) inhibitors of the formula

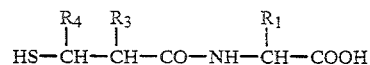

wherein $R_3$ and $R_4$ can be hydrogen, lower alkyl or phenylloweralkyl and $R_1$ can be various substituted alkyl groups.

U.S. Pat. No. 4,774,256 discloses analgesic enkephalinase inhibitors of the formula

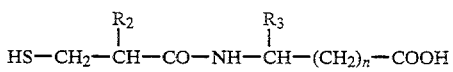

wherein $R_2$ can be cycloloweralkyl lower alkyl, n can be 1-15 and $R_3$ is alkyl, phenylalkyl or heteroarylalkyl. U.K. 2,207,351A discloses compounds of a similar scope as diuretics, natriuretics and blood pressure lowering agents.

U.S. Pat. No. 4,610,816 discloses, inter alia, substituted dipeptide enkephalinase inhibitors of the formula

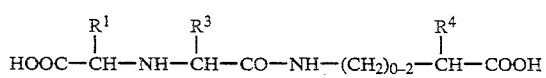

wherein $R^1$ and $R^3$ are preferably phenylethyl and $R^4$ is preferably hydrogen, methyl or benzyl.

German Patent Application 3,819,539 discloses, inter alia, carboxyalkyl compounds of the formula

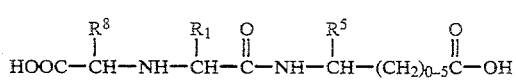

wherein $R_1$ and $R_8$ are preferably benzyl and $R_5$ is preferably hydrogen or lower alkyl.

It is known that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homostasis", *N. Engl. J. Med.*, 314, 13 (1986) pp. 828-834, and M. Cantin et al in "The Heart as an Endocrine Gland", *Scientific American*, 254 (1986) pg. 76-81.

Angiotensin converting enzyme (ACE) inhibitors are another class of drugs known to be effective in treating some types of hypertension. ACE inhibitors are useful in blocking the rise in blood pressure caused by increases in vascular resistance and fluid volume due to the formation of angiotensin II from angiotensin I. For a review of ACE inhibitors, see M. Wyvratt et al., "Recent Developments in the Design of Angiotensin Converting Enzyme Inhibitors" in *Med. Res. Rev.*, 5, No. 4 (1985) pp. 483-531.

SUMMARY OF THE INVENTION

Novel compounds of the present invention are represented by the formula

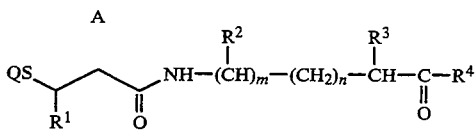

wherein —A— is a 4-,5- or 6-membered alkylene chain substituted with 1 to 3 substituents selected from the group consisting of hydrogen, hydroxy, alkyl or aryl; a 4-, 5- or 6-membered alkenylene chain, wherein I to 3 of the saturated carbon atoms are substituted as defined for the alkylene chain; a 4-,5- or 6-membered hetero-atom-containing chain comprising 2 to 5 carbon atoms and 1 or 2 hetero-atoms selected from the group consisting of oxygen and sulfur, wherein when 2 heteroatoms are present, the heteroatoms are non-adjacent; or an alkylene or hetero-atom-containing chain as defined above wherein said alkylene or hetero-atom-containing chain is substituted with a fused benzene ring;

Q is hydrogen or $R^5CO$—;

$R^1$ is H, alkyl, arylalkyl or aryl;

$R^2$ is H, alkyl, alkoxyalkyl, alkylthioalkyl, aryl, arylalkyl, heteroaryl, heteroarylalkyl, arylalkoxyalkyl or arylalkylthioalkyl;

$R^3$ is H, hydroxy, alkoxy, alkyl, arylalkoxy, alkoxyalkyl, alkylthioalkyl, arylalkoxyalkyl, arylalkylthioalkyl, aryl, heteroaryl, arylalkyl or heteroarylalkyl, or $R^2$ and $R^3$ form an alkylene chain of 1 to 5 carbon atoms, thereby, together with the carbons to which they are attached, completing a 5-, 6- or 7-membered ring;

$R^4$ is hydroxy, alkoxy, aryloxy, arylalkoxy, amino, alkylamino or dialkylamino;

$R^5$ is alkyl or aryl;

m is 0 or 1;

n is 0, 1, 2 or 3;

or a pharmaceutically acceptable salt thereof.

A preferred group of compounds of the present invention is that wherein —A— is alkylene, especially butylene, or alkylene substituted with fused benzene ring, especially wherein —A— and the carbon to which it is attached form an indanyl group. Another preferred group in that wherein $R^2$ is hydrogen, $R^3$ is hydroxy, m is 1 and n is zero. Also preferred are compounds wherein $R^3$ is alkylthioalkyl and m and n are each zero; a preferred alkylthioalkyl group is methylthioethyl. Still another preferred group of compounds of formula I is that wherein $R^2$ and $R^3$ complete a ring, especially a ring formed when m is 1, n is 2 and $R^2$ and $R^3$ form an ethylene group (thereby completing a 6-membered ring).

Other preferred compounds of formula I are those wherein $R^1$ is hydrogen. $R^4$ is preferably hydroxy or ethoxy. Q is preferably hydrogen or acetyl.

The invention also relates to the treatment of cardiovascular diseases with a combination of a mercaptocycloacyl aminoacid of the present invention and an atrial natriuretic factor (ANF) or with a combination of a mercaptocycloacyl aminoacid of the present invention and an ACE inhibitor.

Other aspects of the invention relate to pharmaceutical compositions comprising a mercaptocycloacyl aminoacid of this invention, alone or in combination with an ANF or an ACE inhibitor, and to methods of treatment of cardiovascular diseases comprising administering a mercaptocycloacyl aminoacid of this invention, alone or in combination with an ANF or an ACE inhibitor, to a mammal in need of such treatment.

Still another aspect of this invention relates to a method of treating pain conditions by administering a mercaptocycloacyl aminoacid of this invention, thereby inhibiting the action of endopeptidases in a mammal and eliciting an analgesic effect. Analgesic pharmaceutical compositions comprising said mercaptocycloacyl aminoacid compounds are also contemplated.

An additional aspect of the invention relates to a method of treating nephrotoxicity resulting from immunosuppression therapy by administration of a mercaptocycloacyl aminoacid of this invention.

DETAILED DESCRIPTION

As used herein, the term "alkyl" means straight or branched lower alkyl chains of 1 to 6 carbon atoms and "alkoxy" similarly means lower alkoxy chains of 1 to 6 carbon atoms "Alkylene" as used in the definition of —A—, refers to bivalent alkyl radicals of 4 to 6 carbon atoms, wherein said radicals are derived from normal alkanes by removal of a hydrogen atom from each of two terminal carbon atoms in the chain. The term alkenylene refers to similar bivalent radicals of 4 to 6 carbon atoms having one double bond.

The term "hetero-atom-containing chain" refers to alkylene chains of 4 to 6 carbon atoms in which one or more carbon atoms are replaced by an oxygen or sulfur atom. As is apparent from formula I, the alkylene, alkenylene and hetero-atom-containing chains defining —A— form, together with the carbon to which is attached, a cycloalkyl ring of 5 to 7 carbon atoms, a cycloalkenyl ring of 5 to 7 carbon atom, or a heterocycloalkyl group of 5 to 7 ring members wherein 1 or 2 heteroatom ring members are selected from the group consisting of oxygen and sulfur atoms and wherein the heteroatoms are non-adjacent. Said cycloalkyl groups are cyclopentyl, cyclohexyl and cycloheptyl groups; said cycloalkenyl groups are 2- or -3 cyclopentenyl, 2- or 3-cyclohexenyl, and 2-,3- or 4- cycloheptenyl; said heterocycloalkyl groups are, for example, tetrahydrofuranyl, tetrahydrothiophenyl, tetrahydropyranyl, dioxanyl, dioxolanyl, dithianyl and dithiolanyl.

"Aryl" means a phenyl or naphthyl ring; a phenyl or naphthyl ring substituted with 1-3 substituents selected from the group consisting of alkyl, hydroxy, alkoxy, halo, trifluoromethyl, phenyl, phenoxy and phenylthio.

"Heteroaryl" means aromatic groups having 5 or 6 ring members wherein 1-2 ring members are independently selected from the group consisting of oxygen, nitrogen and sulfur and wherein 1-3 carbon ring members may be substituted with substituents as defined above for aryl. Examples of heteroaryl groups are furanyl, thienyl, pyrrolyl and pyridyl.

All positional isomers of the aryl and heteroayl groups are contemplated, e.g. 2-pyridyl and 3-pyridyl, α-naphthyl and β-naphthyl.

Halo means fluoro, chloro, bromo or iodo radicals.

Certain compounds of the invention are acidic e.g., those compounds which possess a carboxyl group. These compounds form pharmaceutically acceptable salts with inorganic and organic bases. Examples of such salts are the sodium, potassium, calcium and aluminum salts. Also included are salts formed with pharmaceutically acceptable amines such as ammonia, alkyl amines, hydroxy alkyl amines, N-methylglucamine and the like.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formula I have at least one asymmetrical carbon atom and therefore include various stereoisomers. The invention includes all such isomers both in pure form and in admixture, including racemic mixtures.

An aspect of the present invention described above relates to the combination of a compound of formula I with an ANF. As indicated by Needleman et al., a number of ANF have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring ANF's also have been found to have comparable biological activity.

Another aspect of the invention is the administration of a combination of an ACE inhibitor and a compound of formula I.

Examples of ACE inhibitors are those disclosed in the article by Wyvratt et al., cited above, and in the following U.S. patents.: U.S. Pat. Nos. 4,105,776, 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published October 6, 1982 discloses N-substituted-N-carboxyalkylcarbonyl amino carboxyl alkyl glycine derivatives which are said to be angiotensin converting enzyme inhibitors and have the formula

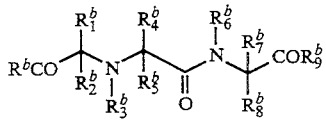

either
(A) $R^b$ and $R_9^b$ are OH, 1–6C alkoxy, 2–6C alkonyloxy, di-(1–6C alkyl) amino-(1–6C) alkoxy, 1–6C hydroxy alkoxy, acylamino- (1–6C) alkoxy, acyloxy-(1–6C)alkoxy, aryloxy, aryloxy-(1–6C)alkoxy, $NH_2$, mono- or di-(1–6C alkyl)amino, hydroxy amino or aryl-(1–6C)alkylamino; $R_1^b$–$R_5^b$, $R_7^b$ and $R_8^b$ are 1–20C alkyl, 2–20C alkonyl, 2–20C alkynyl, aryl, aryl-(1–6C) alkyl having 7–12C or heterocyclyl-(1–6C) alkyl having 7–12C;
$R_6^b$ is cycloalkyl polycycloalkyl partly saturated cycloalkyl or polycycloalkyl, cycloalkyl-(1–6C)alkyl having 3–20C, 6–10C aryl, aryl-(1–6C)alkyl, aryl-(2–6C)alkenyl or aryl-(2–6C) alkynyl; or
$R_2^b$ and $R_3^b$ together with the C and N atoms to which they are attached or $R_3^b$ and $R_5^b$ together with the N and C atoms to which they are attached form an N-heterocycle containing 3–5C or 2–4C and a S atom;

all alkyl, alkonyl and alkynyl are optionally substituted by OH, 1–6C alkoxy, thio(sic), 1–6C alkylthio, $NH_2$, mono- or di(1–6C alkyl)amino, halogen or $NO_2$;

all 'cycloalkyl' groups (including poly and partially unsaturated) are optionally substituted by halogen, 1–6C hydroxy alkyl, 1–6C alkoxy, amino-(1–6C alkyl)amino, di-(1–6C alkyl)amino, SH, 1–6C alkylthio, $NO_2$ or $CF_3$; and aryl groups are optionally substituted by OH, 1–6C alkoxy, $NH_2$, mono- or di-(1–6C alkyl) amino, SH, 1–6C alkylthio, 1–6C hydroxy alkyl, 1–6C aminoalkyl, 1–6C thioalkyl, $NO_2$, halogen, $CF_3$, $OCH_2O$, ureido or guanidino; or (B) $R^b$ and $R_9^b$ are H or 1–6C alkoxy;
$R_1^b$ and $R_2^b$ are H, 1–6C alkyl, aryl-(1–6C) alkyl having 7–12C or heterocyclyl-(1–6C) alkyl having 6–12C;
$R_3^b$–$R_5^b$ and $R_8^b$ are H or 1–6C alkyl;
$R_6^b$ is cycloalkyl polycycloalkyl partly saturated cycloalkyl or polycycloalkyl, cycloalkyl-(1–6C) alkyl having 3–20C, aryl or aryl-(1–6C) alkyl; and
aryl has 6–10C and is optionally substituted by 1–6C alkyl, 2–6C alkonyl, 2–6C alkynyl, OH, 1–6C alkoxy, $NH_2$, mono- or di-(1–6C alkyl) amino, SH, 1–6C alkylthio, 1–6C hydroxy alkyl, 1–6C aminoalkyl, 1–6C thioalkyl, $NO_2$, halogen, $CF_3$, $OCH_2O$, ureido or guanidino;

European Patent Application 0 050 800 published May 5, 1982 discloses carboxy alkyl dipeptides derivatives which are said to be angiotensin converting enzyme inhibitors and have the formula

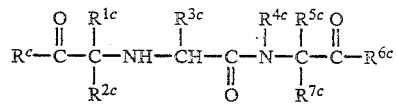

or a pharmaceutically acceptable salt thereof, wherein $R^c$ and $R^{6c}$ are the same or different and are hydroxy, lower alkoxy, lower alkonyloxy, dilower alkylamino lower alkoxy, acylamino lower alkoxy, acyloxy lower alkoxy, aryloxy, aryllower alkoxy, amino, lower alkylamino, dilower alkylamino, hydroxy amino, aryllower alkylamino, or substituted aryloxy or substituted aryllower alkoxy wherein the substituent is methyl, halo or methoxy; $R^{1c}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carboxyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen lower alkyl or $Z^c$, or $R^{4c}$ and $R^{5c}$ taken together form a group represented by $Q^c$, $U^c$, $V^c$, $Y^c$, $D^c$ and $E^c$, wherein;

$Z^c$ is

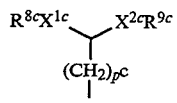

wherein $X^{1c}$ and $X^{2c}$ independent of each other are O, S or CH$_2$, $R^{8c}$ and $R^{9c}$ independent of each other are lower alkyl, lower alkonyl, lower alkynyl, cycloalkyl having 3 to 8 carbon atoms, hydroxy lower alkyl, or —(CH$_2$)$_{n^c}$Ar$^c$, wherein $n^c$ is 0, 1, 2 or 3 and Ar$^c$ is unsubstituted or substituted phenyl, furyl, thienyl or pyridyl, wherein said substituted phenyl, furyl, thienyl or pyridyl groups are substituted with at least one group that is independently selected from C$_1$ to C$_4$ alkyl, lower alkoxy, lower alkylthio, halo, CF$_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$; $Q^c$ is

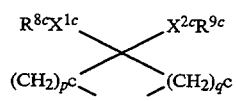

wherein $R^{8c}$, $R^{9c}$, $X^{1c}$ and $X^{2c}$ are as defined above, $p^c$ is 0, 1 or 2, $q^c$ is 0 1 or 2 with the proviso that the sum of $p^c$ and $q^c$ must be 1, 2 or 3, with the proviso that if $p^c$ is 0 then $X^{1c}$ and $X^{2c}$ must be methylene, and with the proviso that if $X^{1c}$ and $X^{2c}$ are methylene then $R^{8c}$ and $R^{9c}$ taken together form a bridge $W^c$, wherein $W^c$ is as defined above; $V^c$ is

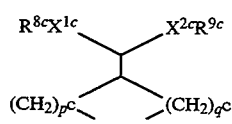

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are CH$_2$ then $R^{8c}$ and $R^{9c}$ taken together form a bridge $W^c$, wherein $W^c$ is as defined above; $U^c$ is

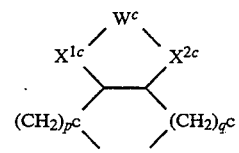

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0 1 or 2, $q^c$ is 0, 1 or 2, with the proviso that the sum of $p^c$ and $q^c$ is 1 or 2, and with the proviso that if $p^c$ is 0, $X^{1c}$ must be CH$_2$;

$Y^c$ is

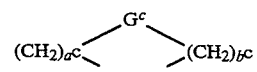

wherein $G^c$ is oxygen, sulfur or CH$_2$, $a^c$ is 2 3 or 4 and $b^c$ is 1, 2, 3, 4 or 5, with the proviso that the sum of $a^c$ and $b^c$ is 5, 6 or 7 or $G^c$ is CH$_2$, $a^c$ is 0, 1, 2 or 3 $b^c$ is 0, 1, 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy;

$D^c$ is

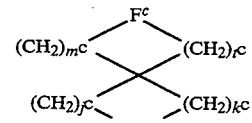

wherein $F^c$ is 0 or S, $j^c$ is 0, 1 or 2 and $k^c$ is 0, 1 or 2, with the proviso that the sum of $j^c$ and $k^c$ must be 1, or 3, and $m^c$ is 1, 2 or 3 and $t^c$ is 1, 2 or 3, with the proviso that the sum of $m^c$ and $t^c$ must be 2, 3 or 4;

$E^c$ is

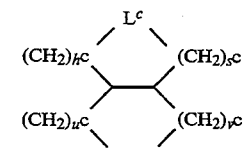

wherein $L^c$ is 0 or S, $u^c$ is 0, 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European Patent Application 0 079 522 published May 25, 1983 discloses N-carboxymethyl(amidino) lysylproline compounds which are said to be angiotensin converting enzyme inhibitors and have the formula where

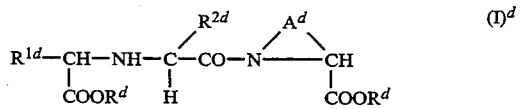

-continued $$R^{1d}-\underset{\underset{COOR^d}{|}}{CH}-NH-\underset{\underset{H}{|}}{\overset{\overset{R^{2d}}{|}}{C}}-CO-\underset{\underset{\underset{COOR^d}{|}}{CHR^{14d}}}{\overset{\overset{R^{3d}}{|}}{N}} \qquad (Ia)^d$$

wherein:
$R^d$ and $R^{2d}$ are independently hydrogen; loweralkyl; aralkyl; or aryl;

$R^{1d}$ is hydrogen; branched or straight chain $C_{1-12}$ alkyl and alkonyl; $C_3$-$C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

$$-\underset{\underset{COOR^d}{|}}{N}\overset{\overset{A^d}{\diagup}}{\underset{\diagdown}{-}}CH \quad \text{is} \quad -N\overset{\overset{X^d-Y^d}{\diagup}}{\underset{\diagdown}{-}}\underset{\underset{R^{4d}}{|}}{\overset{|}{C}}(CH)_{nd},$$

[structure with $W^d$, $Z^d$, $R^{6d}$ on benzene ring]

[structure with $W^d$, $Z^d$, $(CH_2)_{nd}$ on cyclohexane ring]

where:
$X^d$ and $Y^d$ taken together are $-CH_2-CH_2-$; $-\underset{\underset{R^{5d}}{|}}{CH}-S-$; $-\underset{\underset{O}{||}}{C}-CH_2-$; $-CH_2-\overset{\overset{O}{||}}{C}-$;

$-\overset{\overset{O}{||}}{C}-O-$; $-\overset{\overset{O}{||}}{C}-S-$; $-CH_2-\underset{\underset{OR^{4d}}{|}}{CH}-$;

$-\overset{\overset{O}{||}}{C}-\underset{\underset{R^{4d}}{|}}{N}-$; or $-CH_2-\underset{\underset{R^{5d}}{|}}{\overset{\overset{R^{4d}}{|}}{C}}-R^{5d}$;

$R^{4d}$ is hydrogen; loweralkyl; aryl; Substituted aryl;
$R^{5d}$ is hydrogen; loweralkyl; aryl or substituted aryl;
$n^d$ is 1 to 3;
$W^d$ is absent;

$-CH_2-$; or $-\overset{\overset{O}{||}}{C}-$;

$R^{7d}$ is $-(CH_2)_{m^d}$, where $m^d$ is 0 to 2, provided that $m^d$ may not be 0 and $W^d$ may not be absent at the same time; and
$R^{6d}$ is hydrogen; loweralkyl; halo; or $OR^{4d}$;
$R^{2d}$ $-(CH_2)_{r^d}-B^d-(CH_2)_{h d}$ $s^d-NR^{7d}R^{15d}$
where
$r^d$ and $s^d$ are independently 0 to 3;
$B^d$ is absent; $-O-$; $-S-$; or $-NR^{8d}$;
where $R^{8d}$ is hydrogen; loweralkyl; alkanoyl; or aroyl; and
$R^{7d}$ is $-\overset{\overset{NR^{11d}}{||}}{C}-R^{9d};$ $-\overset{\overset{NR^{11d}}{||}}{C}-NHR^{10d};$ or $-\overset{\overset{N-J^d}{||}}{\underset{\underset{K^d}{|}}{C}}-R^{12d}$ where
$R^{9d}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10d}$ is hydrogen; loweralkyl; aryl; or amidino;
$R^{11d}$ hydrogen; loweralkyl; cyano; amidino; aryl; aroyl; loweralkanoyl;

$-\overset{\overset{O}{||}}{C}-NHR^{13d};$ $-\overset{\overset{O}{||}}{C}-OR^{13d};$ $-NO_2$;

$-SO_2NH_2$; or $SO_2R^{13d}$;

$R^{12d}$ is hydrogen; loweralkyl; halo; aralkyl; amino; cyano; mono- or diloweralkylamino; or $OR^{4d}$;
$R^{13d}$ is hydrogen; loweralkyl; or aryl;
$R^{15d}$ is hydrogen; lower alkyl; aralkyl; or aryl;

$-\overset{\overset{N-J^d}{||}}{\underset{\underset{K^d}{|}}{C}}-R^{12d}$ constitute a basic heterocycle of 5 or 6 atoms or benzofused analogs thereof and optionally containing 1-3 N atoms, an oxygen, a sulfur, an S=O, or an $SO_2$ group optionally substituted by amino, lower alkyl amino, diloweralkyl amino, lower alkoxy, or aralkyl groups;
$R^{3d}$ is $C_{3-8}$ cycloalkyl and benzofused $C_{3-8}$ cycloalkyl; perhydrobenzofused $C_{3-8}$ cycloalkyl; aryl; substituted aryl; hetaryl; substituted heteroaryl;
$R^{14d}$ is hydrogen or loweralkyl; and, a pharmaceutically acceptable salt thereof;

European Patent 79022 published May 18, 1983 discloses N-amino acyl-azabicyclooctane carboxylic acid derivatives which have the formula $$X^e-\underset{\underset{Z^e}{|}}{\overset{\overset{Y^e}{|}}{C}}-CH_2-\underset{\underset{COOR_{2e}}{|}}{CH}-NH-\underset{\underset{R_{1e}}{|}}{CH}-CO-N\underset{\underset{HOOC}{\diagdown}}{\overset{\overset{1}{\diagup}}{-}}\overset{\overset{5}{\diagdown}}{\underset{3}{}}$$

hydrogen atoms at ring positions 1 and 5 are cis to each other and the 3-carboxy group has the endo orientation;

$R_1^e$ is H, allyl, vinyl or the side chain of an optionally protected naturally occurring α-amino acid;

$R_2^e$ is H, 1-6C alkyl, 2-6C alkonyl or aryl(1-4C alkyl);

$Y^e$ is H or OH and $Z^e$ is H, or $Y^e$ and $Z^e$ together oxygen;

$X^e$ is 1-6C alkyl, 2-6C alkonyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl);

European Patent 46953 published Mar. 10, 1982 discloses N-amino acyl-indoline and tetrahydro isoguinoline carboxylic acids which are angiotensin coverting enzyme inhibitors and have the formula

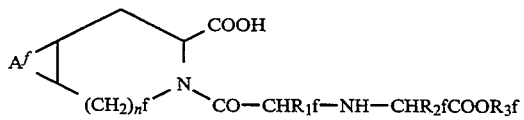

$n^f$ is 0 or 1;

is a benzene or cyclohexane ring:

$R_1^f$ and $R_2^f$ are each 1-6C alkyl, 2-6C alkonyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^f$ and $R_2^f$ groups are optionally substituted, $R_3^f$ is H, 1-6C alkyl, 2-6C alkonyl or 7-14C aralkyl.

The following Table II lists ACE inhibitors preferred for use in the combination of this invention.

TABLE II

| PREFERRED AGE INHIBITORS |
| --- |
| $\begin{array}{cccc} \text{COOR}_1 & \text{R}_2 & \text{O} \\ | & | & \| \\ \text{R}-\text{CH}-\text{NH}-\text{CH}-\text{C}-\text{R}_3 \end{array}$ |

| | R | $R_1$ | $R_2$ | $R_3$ |
| --- | --- | --- | --- | --- |
| spirapril | $C_6H_5CH_2CH_2-$ | Et | $CH_3$ | (dithiolane-proline structure) |
| enalapril | $C_6H_5CH_2CH_2-$ | Et | $CH_3$ | prolyl |
| ramipril | $C_6H_5CH_2CH_2-$ | Et | $CH_3$ | (bicyclic cyclopentane-pyrrolidine structure) |
| perindopril | $CH_3CH_2CH_2-$ | Et | $CH_3$ | (octahydroindole structure) |
| indolapril | $C_6H_5CH_2CH_2-$ | Et | $CH_3$ | (octahydroindole structure) |
| lysinopril | $C_6H_5CH_2CH_2-$ | H | $NH_2(CH_2)_4-$ | prolyl |
| quinapril | $C_6H_5CH_2CH_2-$ | Et | $CH_3$ | (tetrahydroisoquinoline structure) |

TABLE II-continued
PREFERRED AGE INHIBITORS

| | | | | |
|---|---|---|---|---|
| pentopril (NH=CH₂) | CH₃ | | Et | CH₃ |

$$-N\underset{\phantom{x}}{\diagdown}\text{COOH (with o-substituted phenethyl)}$$

| cilazapril | C₆H₅CH₂CH₂— | H | | |

$$-\overset{R_2}{\underset{|}{CH}}-\overset{O}{\underset{\|}{C}}-R_3 \text{ is } \text{(bicyclic N-N system with COOH)}$$

---

$$RS-CH_2-\overset{CH_3}{\underset{|}{CH}}-\overset{O}{\underset{\|}{C}}-R_2$$

| | R | R₂ |
|---|---|---|
| captopril | H | prolyl |
| zofenopril | C₆H₅CO— | (pyrrolidine with SC₆H₅ substituent, COOH) |
| pivalopril | (CH₃)₃C—C(O)— | (cyclopentyl-N—CH₂·COOH) |

---

$$R-\overset{O}{\underset{\|}{P}}-CH_2-\overset{O}{\underset{\|}{C}}-N\underset{\phantom{x}}{\diagdown}\text{COOH}$$
$$\underset{OR^1}{|}$$

with R² substituent on pyrrolidine ring.

| | R | R¹ | R² |
|---|---|---|---|
| fosinopril | C₆H₅—(CH₂)₄— | (CH₃)₂CH—CH—O—C(O)—CH₂CH₃ | C₆H₅— |

---

The compounds of the present invention can be produced by methods known to those skilled in the art, for example by one or more of the methods described below. Reactive groups not involved in the condensations described below, e.g., carboxy, etc., may be protected by methods standard in peptide chemistry prior to the coupling reactions and subsequently deprotected to obtain the desired products. In the formulae in the following description of the processes, A, Q, $R^1$, $R^2$, $R^3$, $R^4$, m and n are as defined above for formula I, including suitable protection where appropriate.

An acid of formula II can be condensed with an aminoacid of formula III:

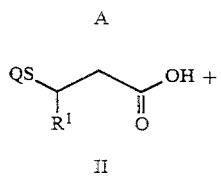

-continued

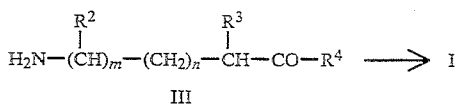

This reaction is well known from peptide chemistry. The reaction can be carried out in the presence of a condensing agent such as 1-(3-dimethylaminopropyl)-3-ethyl-carbodiimide hydrochloride (DEC), dicyclohexylcarbodiimide (DCC), diphenylphosphoryl azide (DPPA) or N,N-disuccinimidyl carbonate in an inert solvent such as dimethylformamide. While, as mentioned above, reactive groups are protected before the coupling reaction is carried out, the carboxy group of compound II can be activated via the intermediacy of active esters such as that derived from 1-hydroxybenzotriazole, the mixed anhydride (derived from a chlorocarbonic acid ester), the chloride or the azide.

It is evident that a compound of formula I obtained by the above process can be transformed into another compound of formula I by methods known in the art.

The starting compounds of formula III are known compounds and/or can be prepared according to known methods. The compounds of formula II can, for example, be prepared by reaction of a dianion of a compound of formula IV with formaldehyde, followed by treatment with methanesulfonyl chloride, replacement with a mercapto group and deprotection of the carboxyl group:

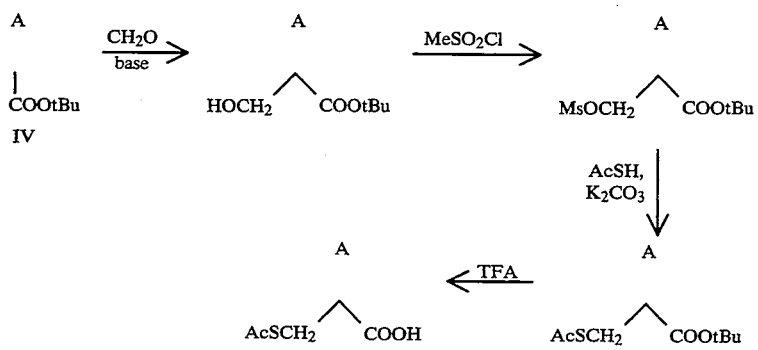

wherein TFA is trifluoroacetic acid and suitable bases are strong bases such as lithium diisopropylamide (LDA), sodium hexamethyldisilazide and lithium tetramethyl piperidide. These processes can be carried out in an inert solvent such as THF at temperatures from −78° C. to room temperature.

For compounds of formula III wherein $R^3$ is hydroxy, it may be desirable to protect such a group during the reaction with II, e.g. with a t-butoxycarbonyl or benzyloxycarbonyl group.

The above processes can be followed by removing protecting groups by known methods. Protected mercapto and carboxy groups, e.g. when $R^4$ is alkoxy (e.g., methoxy, ethoxy, or tert. butyloxy) or benzyloxy and Q is acetyl or benzoyl, are deprotected by conventional means. For example, an acetyl or benzoyl group can be removed by treating with sodium hydroxide, then acidifying with HCl.

We have found that the novel compounds of the present invention are effective in treating cardiovascular disorders such as congestive heart failure, edema, renal insufficiency and various types of hypertension, particularly volume expanded hypertension. These novel compounds enhance both the magnitude and duration of the antihypertensive and natriuretic effects of endogenous ANF. Administration of a combination of a mercaptocycloacyl aminoacid and an ACE inhibitor provides an antihypertensive effect greater than either the mercaptocycloacyl aminoacid or ACE inhibitor alone. Administration of a combination of a mercaptocycloacyl aminoacid of formula I and an exogenous ANF or ACE inhibitor is therefore particularly useful in treating hypertension.

In addition to the compound aspect, the present invention therefore also relates to treating cardiovascular disorders with a mercaptocycloacyl aminoacid of formula I or with a mercaptocycloacyl aminoacid of formula I in combination with an ANF or an ACE inhibitor, which methods comprise administering to a mammal in need of such treatment an amount of the mercaptocycloacyl aminoacid or an amount of a combination of a mercaptocycloacyl aminoacid and ANF or ACE inhibitor effective to treat hypertension, congestive heart failure, edema or renal insuffiency. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral mercaptocycloacyl aminoacid/oral ANF, oral mercaptocycloacyl aminoacid/parenteral ACE inhibitor, parenteral mercaptocycloacyl aminoacid/oral ANF, parenteral mercaptocycloacyl aminoacid/parenteral ACE inhibitor.

When the components of a combination of a mercaptocycloacyl aminoacid and an ANF are administered separately, it is preferred that the mercaptocycloacyl aminoacid be administered first.

The present invention also relates to a pharmaceutical composition comprising a mercaptocycloacyl aminoacid for use in treating hypertension, congestive heart failure, edema or renal insufficiency, to a pharmaceutical composition comprising both a mercaptocycloacyl aminoacid and an ANF and to a pharmaceutical composition comprising both a mercaptocycloacyl aminoacid and an ACE inhibitor.

The antihypertensive effect of mercaptocycloacyl aminoacids was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercaptocycloacyl aminoacid and blood pressure was monitored for the next 4 hours.

A similar procedure can be used to determine the effect of mercaptocycloacyl aminoacid in combination with ACE inhibitors.

The antihypertensive effect of mercaptocycloacyl aminoacids in combination with ANF can be determined according to the following procedures:

Male spontaneously hypertensive rats (SHR), 16-18 weeks old, 270-350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals are allowed a 90-min equilibration period. The animals first undergo a challenge with an ANF such as atriopeptin II (AP II) or AP2S 30 µg/kg iv and at the end of 60 min. are treated with drug vehicle or a mercaptocycloacyl aminoacid subcutaneously. A second ANF challenge is administered 15 min. later and blood pressure is monitored for the next 90 min.

The antihypertensive effect in SHR of mercaptocycloacyl aminoacids and ACE inhibitors, alone and in combination, can be determined as follows:

Animals are prepared for blood pressure measurement as described above. After stabilization, animals are dosed subcutaneously or orally with test drugs or placebo and blood pressure is monitored for the next 4 hr.

The compounds having structural formula I have also been found to inhibit the activity of enzymes designated enkephalinases. The compounds are particularly useful for the inhibition of enkephalinase A, which is derived from the striata of both rats and humans. In in vitro tests, using test procedures for enkephalinase A inhibition well known to those skilled in the art, selected compounds having structural formula I have been found to inhibit the activity of the aforementioned enzyme. Therefore, the present invention also relates to a method of inhibiting the action of enkephalinases in a mammal thereby to elicit an analgesic effect with a compound of formula I, and to analgesic pharmaceutical compositions comprising compounds of formula I.

The use of atrial natriuretic peptides in the treatment of nephrotoxicity associated with the immunosuppressive cyclosporin was reported by Capasso et al. in the *American Journal of Hypertension*, 3, 3 (1990), p. 204–210. Since compounds of this invention enhance endogenous ANF, they can be used alone to treat hephrotoxicity, or they can be administered in combination The compositions of this invention comprise a mercaptocycloacyl aminoacid or a mercaptocycloacyl aminoacid and an ANF or a mercaptocycloacyl aminoacid and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily dose of the compound or combinations of this invention for treatment of hypertension, congestive heart failure, edema or renal insufficiency is as follows: for mercaptocycloacyl aminoacids alone the typical dosage is 1 to 100 mg/kg of mammalian weight per day administered in single or divided dosages; for the combination of mercaptocycloacyl aminoacid and an ANF, the typical dosage is 1 to 100 mg of mercaptocycloacyl aminoacid/kg mammalian weight per day in single or divided dosages plus 0.001 to 0.1 mg ANF/kg of mammalian weight per day, in single or divided dosages, and for the combination of mercaptocycloacyl aminoacid and an ACE inhibitor, the typical dosage is 1 to 100 mg of mercaptocycloacyl aminoacid/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension, congestive heart failure, edema or renal insufficiency, the compounds or combinations of this invention may be administered to patients in a dosage range as follows: for treatment with mercaptocycloacyl aminoacids alone, about 10 to about 500 mg per dose given 1 to 4 times a day, giving a total daily dose of about 10 to 2000 mg per day; for the combination of mercaptocycloacyl aminoacid and ANF, about 10 to about 500 mg mercaptocycloacyl aminoacid per dose given 1 to 4 times a day and about 0.001 to about 1 mg ANF given 1 to 6 times a day (total daily dosage range of 10 to 2000 mg day and 0.001 to 6 mg/day, respectively); and for the combination of a mercaptocycloacyl aminoacid and an ACE inhibitor, about 10 to about 500 mg mercaptocycloacyl aminoacid per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 mg/kg. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

For treatment of edema, renal insufficiency or nephrotoxicity associated with immunosuppressive therapy, dosage ranges of the compounds of this invention are the same as for treatment of hypertension with the use of mercaptocycloacyl aminoacids of this invention alone or in combination with ANF.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, anti-oxidants, lubricants, flavoring agents, and the like commonly used in pharmaceutical formulations.

Since the present invention relates to treatment of hypertension with a combination of active ingredients wherein said active ingredients may be administered separately, the invention also relates to combining separate pharmaceutical compositions in kit form. That is, two kits are contemplated, each combining two separate units: a mercaptocycloacyl aminoacid pharmaceutical composition and an ANF pharmaceutical composition in one kit and a mercaptocycloacyl aminoacid pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of methods of preparing compounds of formula I.

EXAMPLE 1

N-[1-(MERCAPTOMETHYL)CYCLOPENTANECARBONYL]-(S)-METHIONINE 1. t-Butyl Cyclopentanecarboxylate: Condense isobutylene (100 ml) into a cooled tube containing cyclopentanecarboxylic acid (25.0 g, 0.22 mol) and t-butanol (4 ml). Add conc. $H_2SO_4$ (1.0 ml), seal and allow to stand for four days. Cool, open the tube and remove excess isobutylene by warming. Partition between $Et_2O$ and 1.0 N $NaHCO_3$, dry, concentrate and distill to obtain the ester as a colorless liquid, b.p. 55°–60° C./0.1 mm.

2. t-Butyl 1-(Hydroxymethyl)cyclopentanecarboxylate: To diisopropylamine (2.12 g, 21.0 mmol) in tetrahydrofuran (THF) (50 ml) at −70° C., add BuLi hexane solution (2.5M, 8.3 ml, 21.0 mmol). Allow to warm to 0° C., cool again and add dropwise the ester of step 1 (3.0 g, 18 mmol) in THF (50 ml). Generate formaldehyde gas by heating paraformaldehyde (2.58 g) to 160° C. while passing through a stream of nitrogen. Bubble the gas into the solution, then allow to warm to 25° C. Stir 18 hr, add sat. $NH_4Cl$ (100 ml), then sat. NaCl (100 ml). Extract with $CH_2Cl_2$, dry and concentrate. Dissolve the residue in $Et_2O$, filter and concentrate to obtain the crude hydroxyester as a yellow liquid.

3. t-Butyl 1-(Methanesulfonyloxymethyl)cyclopentanecarboxylate: To the hydroxyester of step 2 (1.5 g, 7.5 mmol) and triethylamine (0.83 g, 8.3 mmol) in $Et_2O$ (50 ml), add dropwise methanesulfonyl chloride (0.98 g, 8.3 mmol) in $Et_2O$ (20 ml). Stir 18hr, wash with $H_2O$, dry and concentrate to obtain the crude sulfonate ester as a yellow oil.

4. t-Butyl 1-(Acetylthiomethyl)cyclopentanecarboxylate: Wash NaH (60% in oil, 0.20 g, 0.12 g pure, 5.0 mmol) with hexane and suspend in dimethylformamide (DMF) (7 ml). Add thiolacetic acid (0.40 g, 5.3 mmol) in DMF (3 ml), then dropwise add the sulfonate ester of step 3 (0.90 g, 3.2 mmol) in DMF (7 ml). Heat at 100° C. for 6 hr, allow to cool and partition with EtOAc and 1.0N HCl. Dry, concentrate, dissolve the residue in $Et_2O$, wash with 1.0N $NaHCO_3$, dry and concentrate. Chromatograph on silica, eluting with 5% $Et_2O$-hexane to obtain the mercapto-ester as a red oil.

5. 1-(Acetylthiomethyl)cyclopentanecarboxylic Acid: Dissolve the mercapto-ester of step 4 (0.38 g, 1.5 mmol) in $CH_2Cl_2$ (10 ml) and add trifluoroacetic acid (10 ml). After 1 hr, remove the solvents to obtain the title acid.

6. N-[1-(Acetylthiomethyl)cyclopentanecarbonyl]-(S)-methionine Ethyl Ester: Combine the acid of step 5 (0.29 g, 1.5 mmol), triethylamine (0.29 g, 2.9 mmol), hydroxybenzotriazole (HOBT) (0.22 g, 1.5 mmol) and (S) methionine ethyl ester hydrochloride (0.31 g, 1.5 mmol) in DMF (25 ml). Add 1-(3-dimethylaminopropyl)-3-ethylcarbodiimide hydrochloride (DEC) (0.28 g, 1.5 mmol). Stir 64 hr, partition between EtOAc and $H_2O$, dry the EtOAc layer and concentrate. Chromatograph on silica, eluting with 1:1 $Et_2O$-hexane to obtain the ester as a solid, m.p. 40°–2° C., $[\alpha]^D_{26} = -36.6°$ (EtOH)

7. To the ester of step 6 (0.20 g, 0.55 mmol) in EtOH (10 ml), add 1.0N NaOH (2.0 ml). Stir 1.5 hr, concentrate and add 1.0N HCl (2.0 ml). Extract with EtOAc, dry and concentrate to obtain the title acid, m.p 85°–7° C., $[\alpha]^D_{26} = -15.7°$ (EtOH).

EXAMPLE 2

4-CIS-[1-(MERCAPTOMETHYL)CYCLOPENTANECARBONYLAMINO]-CYCLOHEXANECARBOXYLIC ACID 1. 1-(Acetylthiomethyl)cyclopentanecarboxylic Acid: Prepare the t-butyl ester as in Example 1, step 4, except employing $K_2CO_3$ as base. Convert to the acid as in Example 1, step 5.

2. Ethyl 4-cis-[1-(Acetylthiomethyl)cyclopentanecarbonylamino]cyclohexanecarboxylate: Combine the acid of step 1 (0.40 g, 2.1 mmol), triethylamine (0.42 g, 4.2 mmol), HOBT (0.32 g, 2.4 mmol) and ethyl cis-4-aminocyclohexanecarboxylate hydrochloride (0.44 g, 2.1 mmol) in DMF (30 ml). Add DEC (0.40 g, 2.1 mmol), stir 18hr, partition between EtOAc and 1.0N HCl, dry and concentrate. Chromatograph on silica, eluting with $Et_2O$-hexane 1:1 to obtain the ester as solid, m.p. 72°–3° C.

3. To the ester of step 2 (0.30 g, 0.84 mmol) in EtOH (9 ml), add 1.0N NaOH (3.0 ml). Stir 18 hr, concentrate and add 1.0N HCl (3.0 ml). Extract with EtOAc, dry and concentrate to obtain the title acid, m.p. 173°–4° C.

EXAMPLE 3

N-[1-ACETYLTHIOMETHYL)CYCLOPENTANECARBONYL]-(S)-ISOSERINE ETHYL ESTER

Combine the acid of Example 2, step I (0.35 g, 1.9 mmol), triethylamine (0.28 g, 2.8 mmol), HOBT (0.28 g, 1.9 mmol) and (S)-isoserine ethyl ester hydrochloride (0.31 g, 1.9 mmol) in DMF (40 ml). Add DEC (0.39 g, 2.0 mmol), stir 8 hr, partition between EtOAc and $H_2O$, wash with 1.0N HCl, then 1.0N $NaHCO_3$, dry and concentrate. Chromatograph on silica, eluting with Et$_2$O to obtain the ester as an oil, $[\alpha]^D_{26} = +19.9°$ (EtOH)

EXAMPLE 4

N-[2-(MERCAPTOMETHYL)INDAN-2-CARBONYL]-(S)-METHIONINE

1. Indan-2,2-dicarboxylic acid: Combine diethyl indan-2,2-dicarboxylate (21.0 g, 80 mmol) and KOH (12.0 g, 216 mmol) in EtOH (200 ml) and H20 (40 ml). Reflux 75 min, concentrate, dilute with H$_2$O (250 ml) and acidify with conc. HCl. Collect the white solid and dry under vacuum.

2. Indan-2-carboxylic acid: Heat the above in an oil bath at 180°–5° C. until gas evolution from the melt ceases. Allow to cool and collect the solid.

3. t-Butyl Indan-2-carboxlate: Condense isobutylene (100 ml) into a cooled tube containing the acid of step 2 (5.5 g, 34 mmol) and t-butanol (5 ml). Add conc. H$_2$SO$_4$ (1.0 ml), seal and allow to stand 24 hr. Cool, open the tube and remove excess isobutylene by warming. Partition with Et$_2$O and 1.0N NaHCO$_3$, dry and concentrate. Chromatograph on silica, eluting with 5% Et$_2$/hexane to obtain the ester as an oil.

4. t-Butyl 2-(Hydroxymethyl)indan-2-carboxylate: To diisopropylamine (2.82 g, 28.0 mmol) in THF (50 ml) at −70° C., add BuLi·hexane solution (2.5M, 11.0 ml, 28 mmol). Allow to warm to 0° C., cool again, and add dropwise the ester of step 3 (6.0 g, 25 mmol) in THF (25 ml). Generate formaldehyde gas by heating paraformaldehyde (3.5 g) to 160° C. while passing through a stream of nitrogen. Bubble the gas into the solution, then allow to warm to 25° C. Stir 18hr, add sat. NH$_4$Cl (10 ml), then sat. NaCl (100 ml). Extract with CH$_2$Cl$_2$, dry and concentrate. Recrystallize to obtain the title compound as white solid, m.p. 68°–9° C.

5. t-Butyl 2-(Methanesulfonyloxymethyl)indan-2-carboxylate: To the hydroxyester of step 4 (4.30 g, 17.3 mmol) and triethylamine (1.91 g, 19.1 mmol) in Et$_2$O (70 ml), add dropwise methanesulfonyl chloride (2.26 g, 19.0 mmol). Stir 30 min, wash with H$_2$O, then 1.0N NaHCO$_3$, dry and concentrate. Recrystallize from Et$_2$O-hexane to obtain the sulfonate ester as a pale yellow solid, m.p. 82° C.

6. t-Butyl 2-(Acetylthiomethyl)indan-2-carboxylate: Combine the sulfonate ester of step 5 (4.8 g, 15 mmol) thiolacetic acid (2.35 g, 31mmol) and K$_2$CO$_3$ (2.03 g, 15 mmol) in DMF (30 ml). Heat at 100° C. for 2hr, allow to cool 18 hr and partition with EtOAc and 1.0N HCl. Dry, concentrate, dissolve the residue in Et$_2$O, wash with 1.0N NaHCO$_3$, dry and concentrate. Chromatograph on silica, eluting with 5% Et$_2$O-hexane to obtain the mercapto-ester as a red oil.

7. 2-(Acetylthiomethyl)indan-2-carboxylic Acid: Dissolve the mercapto-ester of step 6 (1.80 g, 5.88 mmol) in CH$_2$Cl$_2$ (40 ml) and add trifluoroacetic acid (40 ml). After 18 hr, remove the solvents to obtain a brown solid.

8. N-[2-(Acetylthiomethyl)indan-2-carbonyl]-(S)-methionine Ethyl Ester: Combine the acid of step 7 (0.50 g, 2.1 mmol), triethylamine (0.63 g, 6.3 mmol), HOBT (0.32 g, 2.1 mmol) and (S)-methionine ethyl ester hydrochloride (0.45 g, 2.1 mmol) in DMF (20 ml). Add DEC 0.44 g, 2.3 mmol). Stir 18hr, partition between EtOAc and H$_2$O, wash with 1.0N HCl, then 1.0N NaHCO$_3$, dry and concentrate. Chromatograph on silica, eluting with 1:1 Et$_2$O-hexane to obtain a solid, m.p. 42°–4° C., $[\alpha]^D_{26} = -29.5°$ (EtOH).

9. To the ester of step 8 (0.30 g, 0.73 mmol) in EtOH (15 ml), add 1.0N NaOH (3.0 ml). Stir 3 hr, concentrate and add 1.0N HCl (3.0 ml). Extract with EtOAc, dry and concentrate to obtain the title acid as a gum, $[\alpha]^D_{26} = -17.6°$ (EtOH).

EXAMPLE 5

4-CIS-[2-(MERCAPTOMETHYL)INDAN-Z-CARBONYLAMINO]-CYCLOHEXANECARBOXYLIC ACID

1. Ethyl 4-cis-[2-Acetylthiomethyl)indan-2-carbonylamino]cyclohexanecarboxylate: Combine the acid of Example 4, step 7 (0.50 g, 2.1 mmol), triethylamine (0.63 g, 63 mmol), HOBT (0.32 g, 2.1 mmol) and ethyl cis-4-aminocyclohexanecarboxylate hydrochloride (0.43 g, 2.1 mmol) in DMF (20 ml). Add DEC (0.44 g, 2.3 mmol). Stir 2hr, partition between EtOAc and H$_2$O, wash with 1.0N HCl, then 1.0N NaHCO$_3$, dry and concentrate. Chromatograph on silica, eluting with 1:1 Et$_2$O-hexane to obtain a solid, m.p. 98° C.

2. To the ester of step 1 (0.30 g, 0.74 mmol) in EtOH (15 ml), add 1.0N NaOH (3.0 ml). Stir 18 hr, concentrate and add 1.0N HCl (3.0 ml). Collect the solid, dissolve in EtOAc, dry and concentrate to obtain the title acid, m.p. 171°–3° C.

EXAMPLE 6

N-[2-(ACETYLTHIOMETHYL)INDAN-2-CARBONYL]-(S)-ISOSERINE ETHYL ESTER

Combine the acid of Example 4, step 7 (0.30 g, 1.3 mmol), triethylamine (0.19 g, 2.0mmol), HOBT (0.20 g, 1.3 mmol) and (S)-isoserine ethyl ester hydrochloride (0.22 g, 1.3 mmol) in DMF (15 ml). Add DEC (0.27 g, 1.4 mmol). Stir 18 hr, partition between EtOAc and H$_2$O wash with 1.0N NaHCO$_3$, dry and concentrate. Chromatograph on silica, eluting with MeOH/CH$_2$Cl$_2$ to obtain the ester as an oil, MS: M+1=66.

EXAMPLE 7

N-[2-(MERCAPTOMETHYL)INDAN-2-CARBONYL]-(S)-ISOSERINE

To the product of Example 6 (0.19 g, 0.52 mmol) in ETOH, add 1.0N NaOH (3.0 ml), stir 45 min and add 1.0N HCl (3.0 ml). Extract with EtOAc, dry and concentrate to obtain the title compound as a gum, $[\alpha]^D_{26} = +2.8°$ (EtOH)

The following formulations exemplify some of the dosage forms of the compositions of this invention. In each, the term "active compound" designates a compound of formula I, preferably N-[1-(acetylthiomethyl) cyclopentanecarbonyl]-(S)-methionine ethyl ester. However, this compound may be replaced by equally effective amounts of other compounds of formula I.

Pharmaceutical Dosage Form Examples

Example A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |

-continued

| No. | Ingredient | mg/tablet | mg/tablet |
|---|---|---|---|
|  | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. compress the mixture to appropriate size and weight on a suitable tablet machine.

Example B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | TOTAL | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

Parenteral Preparation

| Ingredient | mg/vial | mg/vial |
|---|---|---|
| Active Compound Sterile Powder | 100 | 500 |

For reconstitution add sterile water for injection or bacteriostatic water for injection.

We claim:

1. A compound represented by the formula

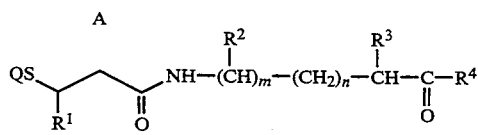

wherein —A— is a 4-, 5- or 6-membered alkylene chain substituted with 1 to 3 substituents selected from the group consisting of hydrogen, hydroxy, alkyl or aryl; a 4-, 5- or 6-membered alkenylene chain, wherein 1 to 3 of the saturated carbon atoms are substituted as defined for the alkylene chain; or an alkylene chain as defined above wherein said alkylene chain is substituted with a fused benzene ring;

Q is hydrogen or $R^5CO$—;

$R^1$ is H, alkyl, arylalkyl or aryl;

$R^2$ is H, alkyl, alkoxyalkyl, alkylthioalkyl, aryl, arylalkyl, arylalkoxyalkyl or arylalkylthioalkyl;

$R^3$ is H, hydroxy, alkoxy, alkyl, arylalkoxy, alkoxyalkyl, alkylthioalkyl, arylalkoxyalkyl, arylalkylthioalkyl, aryl, or arylalkyl or $R^2$ and $R^3$ form an alkylene chain of 1 to 5 carbon atoms, thereby, together with the carbon to which they are attached, completing a 5- 6- or 7-membered ring;

$R^4$ is hydroxy, alkoxy, aryloxy, arylalkoxy, amino, alkylamino or dialkylamino;

$R^5$ is alkyl or aryl;

m is 0 or 1;

n is 0, 1,2 or 3;

or a pharmaceutically acceptable salt thereof.

2. A compound of claim 1 wherein Q is hydrogen or acetyl.

3. A compound of claim 1 wherein —A— is alkylene or alkylene substituted with a fused benzene ring.

4. A compound of claim 1 wherein $R^1$ is hydrogen.

5. A compound as claimed in claim 1 or 3 wherein $R^2$ is hydrogen, $R^3$ in hydroxy, m is 1 and n is zero.

6. A compound as claimed in claim 1 or 3 wherein m and n are each zero and $R^3$ is alkylthioalkyl.

7. A compound as claimed in claim 1 wherein $R^2$ and $R^3$ form an alkylene chain of 1 to 5 carbon atoms, thereby, together with the carbons to which they are attached, completing a 5-, 6- or 7-membered ring.

8. A compound of claim 1 wherein $R^4$ is hydroxy or alkoxy.

9. A compound of claim 1 having the formula:

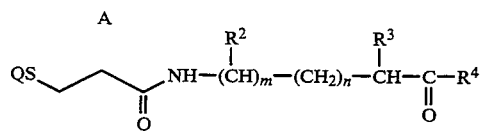

wherein Q, A, $R^2$, $R^3$, $R^4$, m and n have the following values:

| Q | A | $R^2$ | $R^3$ | $R^4$ | m | n |
|---|---|---|---|---|---|---|
| H | —$C_4H_8$— | — | $CH_3S(CH_2)_2$— | OH | 0 | 0 |
| Ac | —$C_4H_8$— | — | $CH_3S(CH_2)_2$— | OEt | 0 | 0 |
| H | —$C_4H_8$— | — | —$(CH_2)_2$— | OH | 1 | 2 |
| Ac | —$C_4H_8$— | — | —$(CH_2)_2$— | OEt | 1 | 2 |
| Ac | —$C_4H_8$— | H | OH |  | OEt | 1 | 0 |
| H | ⌬ | — | $CH_3S(CH_2)_2$— | OH | 0 | 0 |
| Ac | ⌬ | — | $CH_3S(CH_2)_2$— | OEt | 0 | 0 |
| H | ⌬ | — | —$(CH_2)_2$— | OH | 1 | 2 |
| Ac | ⌬ | — | —$(CH_2)_2$— | OEt | 1 | 2 |
| Ac | ⌬ | H | OH |  | OEt | 1 | 0 |

-continued

| Q | A | R² | R³ | R⁴ | m | n |
|---|---|---|---|---|---|---|
| H | 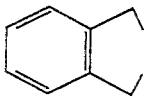 | H | OH | OH | 1 | 0 | wherein Ac is acetyl and Et is ethyl.

10. A pharmaceutical composition for treating hypertension comprising an effective amount of a compound of claim 1 in a pharmaceutically acceptable carrier.

11. A method for treating hypertension in mammals comprising administering to a mammal in need of such treatment an effective amount of a compound of claim 1.

* * * * *

UNITED STATES PATENT AND TRADEMARK OFFICE
CERTIFICATE OF CORRECTION

PATENT NO. : 5,407,960
DATED : APRIL 18, 1995
INVENTOR(S) : BERNARD R. NEUSTADT

It is certified that error appears in the above-identified patent and that said Letters Patent is hereby corrected as shown below:

Title page, item [57], col. 2,

In each of the following places: in the Abstract, in column 3, line 1, and in claim 1, change the portion of the formula reading

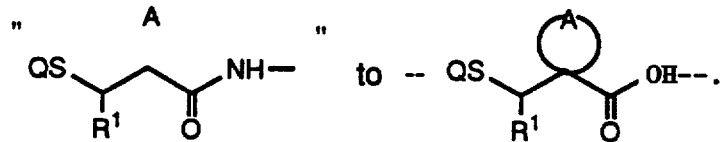

In column 13, line 65, change the formula

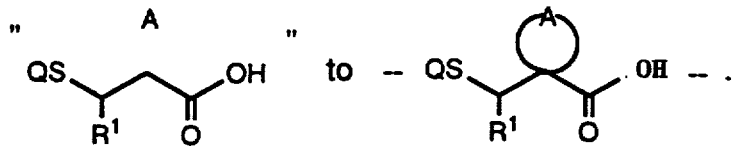

In column 15, in the reaction scheme, change formula IV from

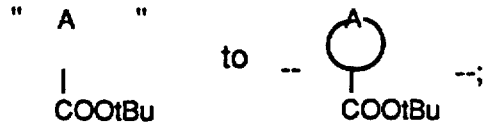

UNITED STATES PATENT AND TRADEMARK OFFICE
CERTIFICATE OF CORRECTION

PATENT NO. : 5,407,960
DATED : APRIL 18, 1995
INVENTOR(S) : BERNARD R. NEUSTADT

It is certified that error appears in the above-identified patent and that said Letters Patent is hereby corrected as shown below:

and in each of the other formulae in the reaction scheme, change the portion of the formula reading

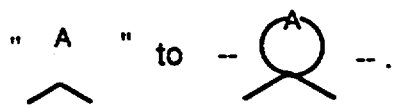

In column 24, claim 9, change the portion of the formula reading

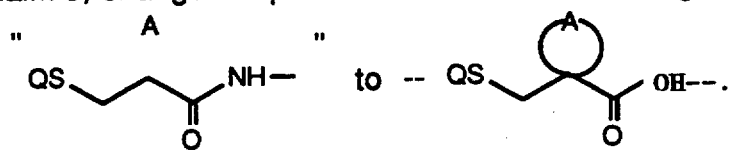

Signed and Sealed this

Twenty-sixth Day of September, 1995

*Attest:*

BRUCE LEHMAN

*Attesting Officer*     *Commissioner of Patents and Trademarks*